United States Patent
You et al.

(10) Patent No.: US 12,383,535 B2
(45) Date of Patent: Aug. 12, 2025

(54) HYDROGEN PEROXIDE-RESPONSIVE KEAP1-NRF2 PPI INHIBITOR PRODRUG, AND PREPARATION METHOD THEREFOR

(71) Applicant: CHINA PHARMACEUTICAL UNIVERSITY, Suzhou (CN)

(72) Inventors: Qidong You, Suzhou (CN); Zhengyu Jiang, Suzhou (CN); Mengchen Lu, Suzhou (CN); Xian Zhang, Suzhou (CN); Jing Zhao, Suzhou (CN); Xiaoke Guo, Suzhou (CN); Xiaoli Xu, Suzhou (CN); Lei Wang, Suzhou (CN)

(73) Assignee: CHINA PHARMACEUTICAL UNIVERSITY, Jiangsu (CN)

( * ) Notice: Subject to any disclaimer, the term of this patent is extended or adjusted under 35 U.S.C. 154(b) by 897 days.

(21) Appl. No.: 17/623,882

(22) PCT Filed: Nov. 16, 2020

(86) PCT No.: PCT/CN2020/128961
§ 371 (c)(1),
(2) Date: Dec. 30, 2021

(87) PCT Pub. No.: WO2021/104072
PCT Pub. Date: Jun. 3, 2021

(65) Prior Publication Data
US 2022/0401419 A1    Dec. 22, 2022

(30) Foreign Application Priority Data
Nov. 28, 2019 (CN) .......................... 201911195753.1

(51) Int. Cl.
*A61K 31/426* (2006.01)
*A61P 29/00* (2006.01)
*C07D 277/14* (2006.01)

(52) U.S. Cl.
CPC ............ *A61K 31/426* (2013.01); *A61P 29/00* (2018.01); *C07D 277/14* (2013.01)

(58) Field of Classification Search
CPC ...... C07D 277/14; A61K 31/426; A61P 29/00
See application file for complete search history.

(56) References Cited

FOREIGN PATENT DOCUMENTS

| CN | 108112251 | 6/2018 | |
|---|---|---|---|
| CN | 108752245 | 11/2018 | |
| CN | 110845435 | 2/2020 | |
| WO | WO-2021104072 A1 * | 6/2021 | ........... A61K 31/426 |

OTHER PUBLICATIONS

Zheng-Yu Jiang et al., "Discovery and Development of Kelch-like ECH-Associated Protein 1. Nuclear Factor Erythroid 2-Related Factor 2 (KEAP1:NRF2) Protein-Protein Interaction Inhibitors: Achievements, Challenges, and Future Directions," Journal of Medicinal Chemistry, vol. 59, No. 24, Oct. 2016, pp. 10837-10858.

Meng-Chen Lu et al., "An inhibitor of the Keap1-Nrf2 protein-protein interaction protects NCM460 colonic cells and alleviates experimental colitis," Scientific Reports, vol. 6, Article No. 26585, May 2016, pp. 1-13.

"International Search Report (Form PCT/ISA/210) of PCT/CN2020/128961," mailed on Jan. 27, 2021, with English translation thereof, pp. 1-6.

* cited by examiner

*Primary Examiner* — Kevin E Weddington
(74) *Attorney, Agent, or Firm* — JCIP GLOBAL INC.

(57) ABSTRACT

The present application relates to a hydrogen peroxide-responsive Keap1-Nrf2 PPI inhibitor prodrug, and a preparation method therefor. The hydrogen peroxide-responsive Keap1-Nrf2 PPI inhibitor prodrug pro2 has a chemical structure as shown below. By modifying a key carboxyl pharmacophore in a Keap1-Nrf2 inhibitor with a $H_2O_2$-responsive thiazolidinone moiety, a novel ROS-responsive antioxidant prodrug pro2 is synthesized. The $H_2O_2$ activated prodrug pro2 can simultaneously achieve targeted activation of Nrf2 and enhancement of therapeutic efficacy in the body. The prodrug is based on the concept of ROS activation-ROS clearance therapy, is the first example of a $H_2O_2$-responsive prodrug suitable for oral administration, and is expected to be used clinically by virtue of the characteristics of druggability and high targeting ability.

7 Claims, 6 Drawing Sheets
Specification includes a Sequence Listing.

HYDROGEN PEROXIDE-RESPONSIVE KEAP1-NRF2 PPI INHIBITOR PRODRUG, AND PREPARATION METHOD THEREFOR

CROSS-REFERENCE TO RELATED APPLICATION

This application is a 371 of international application of PCT application serial no. PCT/CN2020/128961, filed on Nov. 16, 2020, which claims the priority benefit of China application no. 201911195753.1, filed on Nov. 28, 2019. The entirety of each of the above-mentioned patent applications is hereby incorporated by reference herein and made a part of this specification.

TECHNICAL FIELD

The present invention relates to the field of organic synthesis, particularly to a prodrug of Keap1-Nrf2 PPI inhibitor, and more particularly to a prodrug of hydrogen peroxide-responsive Keap1-Nrf2 PPI inhibitor, a method for preparing the same, and pharmaceutical use thereof.

BACKGROUND

Nuclear transcription factor (Nrf2), a major regulator of a variety of cytoprotective responses, plays a key role in the regulation of redox and metabolic homeostasis as well as oxidative stress. Activation of Nrf2 can enhance antioxidant capacity and pose protective effect against oxidative stress and inflammatory injury. Recently, therapeutic targets for protein interaction of Nrf2 and its major negative regulator E3 ubiquitin ligase Kelch-like ECH-associated protein 1 (Keap1) are becoming new strategies for developing drugs for treating chronic diseases. Several PPI inhibitors that effectively disrupt the Keap1-Nrf2 interaction have been reported by several pharmaceutical companies and research institutions. However, these inhibitors still involve risks regarding pharmacokinetics and drug safety. One major difficulty for developing such inhibitors is how to prepare Keap1-Nrf2 PPI inhibitors with suitable cell permeability and pharmacokinetics. All the currently reported inhibitors have molecules with rather high molecular weight and several polar functional groups, and need to interrupt the larger and highly polar Keap1-Nrf2 interface. Such compounds with high potency hi vitro exhibit poor absorption, distribution, metabolism and excretion properties, and relatively low potency in vivo. Safety issues are also a challenge for Keap1-Nrf2 inhibitors, as Nrf2 activation in normal cells can over-enhance the antioxidant system, leading to clearance of ROS, which may interfere with pathological functions of ROS. There is also concern that Nrf2 activators may bring carcinogenic risks. Somatic mutations in KEAP1 and NFE2L2 result in an unrestricted increase in Nrf2 activity, which has been considered to be a driver for several tumors. Therefore, selective inhibition of the Keap1-Nrf2 interaction during oxidative stress is a major challenge, and would greatly facilitate therapeutic application of the inhibitor. Based on the above considerations, it is a two-fold strategy to design a prodrug of Keap1-Nrf2 inhibitor that exposes the carboxyl group upon activation by ROS. It may not only improve the poor cell permeability and pharmacokinetics caused by the polarity and ionizable nature of the carboxylic acid group, but also modify key groups to which Keap1 binds until reaching the target cell, thereby rebalancing the redox state in pathological cells without affecting normal cells.

Hydrogen peroxide ($H_2O_2$) is an uncharged molecule, and belongs to a stable reactive oxygen species (ROS). It is produced endogenously and is ubiquitous in organisms. Physiologically, $H_2O_2$ plays a positive role in redox signaling through reversible redox reactions post-translational modifications. Its level can be regulated by an antioxidant system. However, excessive hydrogen peroxide is closely associated with a variety of pathological conditions, including inflammation, neurodegenerative diseases, and cancer. On the one hand, excessive $H_2O_2$, together with abnormal oxidative stress, contributes to the development of such diseases. On the other hand, excessive $H_2O_2$ in the pathological microenvironment may be an ideal trigger for targeted activation of therapeutic agents. Chang et al. reported a pioneering work with $H_2O_2$-responsive arylboronate triggers, which stimulated rapid development of arylboronate-based $H_2O_2$ probes. Pent et al. used boronate esters or boronic acids as trigger units, developing the first $H_2O_2$-activated DNA cross-linking agents. The chemical stability and high levels of $H_2O_2$ in cancer cells relative to normal cells make it an ideal stimulus for the development of tumor-specific cytotoxins, and a variety of $H_2O_2$-activated anticancer drugs have been discovered.

Recently, increasing evidence from different studies supports the relationship between oxidative stress and the pathogenesis of inflammation, and has inspired researches on $H_2O_2$-responsive cytoprotection and anti-inflammatory agents, including prodrugs of methotrexate and aminopterin for treating rheumatoid arthritis, prodrugs of $H_2S$ donors and CO donors, and prodrugs of neuroprotective angiogenin. However, most of the currently available $H_2O_2$-responsive prodrugs are developed for anticancer treatment, and few of the drugs have proven efficacy in vivo. More importantly, there is still no oral $H_2O_2$-responsive prodrug, which limits the therapeutic use in chronic inflammatory diseases. Thus, the approach can be improved to develop novel $H_2O_2$-responsive prodrugs for oral administration.

SUMMARY OF INVENTION

Purpose: For the defects in the prior art, the present application provides a prodrug of hydrogen peroxide-responsive Keap1-Nrf2 PPI inhibitor, a method for preparing the same, and pharmaceutical use thereof.

Technical Scheme:

A prodrug pro2 of hydrogen peroxide-responsive Keap1-Nrf2 PPI inhibitor having the following structural formula:

The synthetic route of the prodrug pro2 is as follows:

wherein, the reagents and conditions in each step are as follows:
(b) Pd/C, H$_2$, THF, rt, 4 h;
(c) 4-methoxybenzenesulfonyl chloride, Na$_2$CO$_3$, THF, 0° C., 2 h;
(d) 4-methoxybenzenesulfonyl chloride, toluene, pyridine, 100° C., 2 h;
(e) DMF, K$_2$CO$_3$, ethyl bromoacetate, rt, 3 h;
(f) LiOH, MeOH, H$_2$O, 2 h; and
(g) thiazolidin-2-one, DMAP, DCC, DMF, rt, 6 h.

Further, the synthetic route of compound 4 is as follows:

wherein, the reagents and conditions in the step (a) are as follows: NH$_2$OH—HCl, 95% ethanol, MeOH, 60° C., and 2 h.

Use of the prodrug pro2 in preparing an anti-inflammatory drug.

Further, the drug is for oral administration.

Beneficial Effects: In the present invention, a novel ROS-responsive antioxidant prodrug pro2 is synthesized using a H$_2$O$_2$-responsive thiazolidinone moiety to modify a key carboxyl pharmacophore in a Keap1-Nrf2 inhibitor. The H$_2$O$_2$-activated prodrug pro2 can simultaneously achieve targeted activation of Nrf2 and enhancement of therapeutic efficacy in vivo. The prodrug is based on the concept of ROS activation-ROS clearance therapy, is also the first example of a H$_2$O$_2$-responsive prodrug suitable for oral administration, and is expected to be used for preparing anti-inflammatory drugs by virtue of the characteristics of druggability and high targeting ability.

BRIEF DESCRIPTION OF DRAWINGS

(A) of FIG. 4 to (D) of FIG. 4 are graphs showing real-time quantitative PCR analyses of Nrf2 (A), HO-1 (B), NQO1 (C) and GCLM (D) in RAW264.7 cells; (E) of FIG. 4 is a graph showing a western blot assay of Nrf2 targeting proteins in RAW264.7 cells; (F) of FIG. 4 to (I) of FIG. 4 are graphs showing assays of SOD (F), GSH-PX (G), GSH/GSSG (H), and MPO (I) levels in RAW264.7 cells.

(A) of FIG. 5 to (B) of FIG. 5 are graphs showing real-time quantitative PCR analyses of IL-1β (A) and IL-6 (B) in RAW264.7 cells; (C) of FIG. 5 is a graph showing a western blot assay of IL-1β and IL-6 protein levels in RAW264.7 cells; (D) of FIG. 5 to (G) of FIG. 5 are graphs showing concentrations of IL-1β (D), IL-6 (E), TNF-α (F) and NO (G) in the supernatant of a RAW264.7 cell culture.

(A) of FIG. 6 to (D) of FIG. 6 are graphs showing IL-1β (A), IL-6 (B), TNF-α (C) and IFN-γ (D) levels in mouse serum.

DESCRIPTION OF EMBODIMENTS

The material content of the present invention will be described with reference to drawings and examples, which are not intended to limit the scope of the present invention.

The chemical agents used in the present invention are all commercially available, and chemically pure or analytically pure, and may be purified and dried, if necessary, by standard methods. Reactions were monitored by thin layer chromatography on a silica gel plate (GF-254) visible under UV light. Melting points were determined on a Mel-TEMP II melting point analyzer without calibration. $^1$H NMR and $^{13}$C NMR spectroscopic measurements were performed in $CDC_3$ or DMSO-$d_6$ solvents using a Bruker Avance-300 instrument. Tetramethylsilane (TMS) was used as an internal standard and chemical shifts (δ) were expressed in ppm by the residual solvent resonance method ($CDC_3$: 7.26 ppm for $^1$H NMR, and 77.16 ppm for $^{13}$C NMR; DMSO: 2.5 ppm for $^1$H NMR, and 39.5 ppm for $^{13}$C NMR). Multiplicity is abbreviated as follows: s=singlet, d=doublet, t=trap, q=quartet, and m=multiplet. HR-MS spectra were obtained by using a Waters Q-Tof micro mass spectrometer. 100-200 mesh silica gel was used for column chromatography, and the yield refers to the compound obtained by chromatographic and spectral purification. Agilent C18 (4.6 mm×150 mm, 3.5 μm) column was used to determine the purity of compounds (≥95%) by HPLC, a mixture of methanol and water was used as the mobile phase, the flow rate was 0.5 mL/min, and the UV absorbance at 254 nm was monitored.

Example 1. Synthesis and Structure Confirmation of Target Compound

1. Preparation of Intermediates 1.1. Preparation of 4-methoxy-N-(naphthalen-1-yl)benzenesulfonamide (5)

4-Nitronaphthalen-1-amine (4) (3 g, 15.9 mmol) was dissolved in THF and a catalytic amount of palladium on carbon was added to react for 5 h, before the catalyst was removed by filtration through celite. The crude product naphthalene-1,4-diamine was used without further purification. To the filtrate was added 4-methoxybenzenesulfonyl chloride (2.99 g, 14.5 mmol) and sodium carbonate (2.53 g, 23.9 mmol), and the reaction solution was stirred in an ice bath in nitrogen atmosphere for 2 h. After the reaction was complete, sodium carbonate was removed by filtration and the filtrate was collected. Recrystallization was performed in acetonitrile to give a pink solid (3.12 g, 62% yield). $R_f$=0.37 (EA/PE 2:1); m.p. 169-171° C.; $^1$H-NMR (300 MHz, DMSO-$d_6$): δ=9.39 (s, 1H; NH), 8.05-7.93 (m, 1H; Ar—H), 7.93-7.82 (m, 1H; Ar—H), 7.59-7.48 (m, 2H; Ar—H), 7.37-7.26 (m, 2H; Ar—H), 7.02-6.95 (m, 2H; Ar—H), 6.68 (d, J=8.0 Hz, 1H; Ar—H), 6.47 (d, J=8.0 Hz, 1H; Ar—H), 5.80 (s, 2H; $NH_2$), 3.78 (s, 3H; $OCH_3$); HRMS (ESI): m/z $C_{17}H_{16}N_2O_3S+Na^+$: 351.0774 $[M+Na]^+$, molecular weight: 351.0777.

1.2. Preparation of methyl N-(4-aminonaphthalen-1-yl)-N-((4-methoxyphenyl)sulfonyl)glycinate (6)

Compound 5 (3.12 g, 9.4 mmol) was dissolved in DMF (15 mL) and $K_2CO_3$ (3.91 g, 28.3 mmol) was added, followed by adding ethyl bromoacetate (1.59 g, 10.4 mmol). After being stirred at room temperature for 3 h, the reaction solution was diluted with 50 mL of water and filtered to give a crude product. Recrystallization was performed in ethyl acetate/n-hexane to give Compound 6 as a pale pink solid (2.65 g, 67% yield). $R_f$=0.65 (EA/PE 1:1); m.p. 182-183° C.; $^1$H-NMR (300 MHz, DMSO-$d_6$): δ=8.00 (dd, J=22.4, 8.3 Hz, 2H; Ar—H), 7.57 (d, J=8.9 Hz, 2H; Ar—H), 7.38 (dt, 1=13.9, 7.0 Hz, 2H; Ar—H), 7.06 (d, J=8.4 Hz, 2H; Ar—H), 6.77 (d, J=8.1 Hz, 1H; Ar—H), 6.45 (d, J=8.1 Hz, 1H; Ar—H), 5.98 (s, 2H; $NH_2$), 4.37 (s, 2H; $CH_2$), 3.83 (s, 3H; $OCH_3$), 3.55 (s, 3H; $COOCH_3$); HRMS (ESI): m/z calcd for $C_{20}H_{20}N_2O_5S+Na^+$: 423.0985 $[M+Na]^+$; molecular weight: 423.0988.

1.3. Preparation of methyl N-(4-((4-methoxyphenyl)sulfonamido)naphthalen-1-yl)-N-(((4-methoxyphenyl)sulfonyl)glycinate (7)

Compound 6 (2.6 g, 6.49 mmol) was dissolved in toluene (30 mL), and 4-methoxybenzenesulfonyl chloride (1.61 g, 7.79 mmol) and pyridine (0.77 g, 9.74 mmol) were added. The reaction solution was heated to 100° C. in nitrogen atmosphere and stirred for 5 h for reaction. After being cooled to room temperature, the reaction solution was diluted with 30 mL of petroleum ether. The solid was collected by filtration. Recrystallization was performed in acetonitrile to give a grey solid (1.53 g, 41% yield). $R_f$=0.20 (EA/PE 2:1); m.p. 213-215° C.; $^1$H-NMR (300 MHz, DMSO-$d_5$): δ=10.25 (s, 1H; NH), 8.37-8.27 (m, 1H; Ar—H), 8.24-8.08 (m, 1H; Ar—H), 7.61 (td, J=9.1, 4.6 Hz, 6H; Ar—H), 7.19-6.98 (m, 5H; Ar—H), 6.86 (s, 1H, Ar—H), 4.55 (s, 2H; Ar—H), 3.87 (d, J=12.6 Hz, 6H; $OCH_3$), 3.56 (s, 3H; $COOCH_3$); $^{13}$C NMR (75 MHz, DMSO-$d_6$) δ 169.61, 163.45, 163.42, 137.62, 137.50, 133.44, 133.25 (t, J=3.3 Hz), 130.64, 130.39, 129.82, 129.23, 127.33, 126.83, 125.06, 124.87, 114.86, 114.81, 56.22, 53.61, 52.47; HRMS (ESI): m/z $C_{27}H_{26}N_2O_8S_2+H^+$: 571.1203 $[M+H]^+$; molecular weight: 571.1198.

1.4. Preparation of N-(4-((4-methoxyphenyl)sulfonamido)naphthalen-1-yl)-N-((4-methoxyphenyl)sulfonyl)glycine (2)

Compound 7 (1.5 g, 2.62 mmol) was dissolved in methanol (50 mL), and 50 mL of water was added, followed by finally adding LiOH (5 g). The resulting mixture was stirred at room temperature for 2 h, added with 2M HCl to adjust to pH 2, and added with 50 mL of water for dilution. The mixture was filtered to remove the insoluble substances, washed with water (10 mL×5), and then dried in a vacuum desiccator overnight to give Compound 2 as a white solid (1.02 g, 69% yield). $R_f$=0.11 (EA); m.p. 225-227° C.; $^1$H-NMR (300 MHz, DMSO-$d_6$): δ=12.78 (s, 1H; COOH), 10.21 (s, 1H; NH), 8.10 (dd, J=20.4, 7.9 Hz, 2H; Ar—H), 7.63 (dd, J=7.1, 5.2 Hz, 2H; Ar—H), 7.57-7.44 (m, 4H; Ar—H), 7.09-6.93 (m, 6H; Ar—H), 4.35 (s, 2H; $CH_2$), 3.82 (d, J=13.9 Hz, 6H; $OCH_3$); $^{13}$C NMR (75 MHz, DMSO-$d_6$): δ=170.42, 163.28, 162.89, 134.97, 133.82, 133.07, 132.00, 130.37, 130.32, 129.82, 129.45, 127.27, 126.98, 126.76, 125.05, 123.73, 121.77, 114.80, 114.74, 56.18, 56.11, 53.57; HRMS (ESI): m/z $C_{26}H_{24}N_2O_8S_2+NH_4^+$: 574.1312 $[M+NH_4]^+$; molecular weight: 574.1315.

2. Preparation of Target Compound

2.1. Preparation of 4-methoxy-N-(4-(((4-methoxyphenyl)sulfonamido)naphthalen-1-yl)-N-(2-oxo-2-(2-oxothiazolidin-3-yl)ethyl)benzenesulfonamide (pro2)

Compound 2 (0.5 g, 0.90 mmol) was dissolved in DMF (10 mL) at room temperature, and DCC (0.41 g, 1.98 mmol) and DMAP (0.24 g, 1.98 mmol) were added. After 30 min, thiazolidin-2-one (0.186 g, 1.80 mmol) was added, and the mixture was stirred for reaction overnight. After the reaction was complete, the reaction solution was poured into water and extracted with $Et_2O$ (20 mL×3). The organic phases were combined, dried over $Na_2SO_4$ and concentrated in vacuo. The crude product was purified by column chromatography to give a pure product of pro2 as a white solid (0.263 g, 46% yield). $R_f$=0.31 (EA/PE 1:1); m.p. 229-230° C.; $^1$H-NMR (300 MHz, DMSO-$d_6$): δ=10.23 (s, 1H; NH), 8.03 (d, J=8.6 Hz, 2H; Ar—H), 7.65 (d, J=8.5 Hz, 2H; Ar—H), 7.49 (d, J=8.8 Hz, 4H; Ar—H), 7.07 (dd, J=21.6, 8.4 Hz, 6H; Ar—H), 5.00-4.77 (m, 4H; $CH_2$), 3.95 (s, 2H; $CH_2$), 3.86-3.75 (m, 6H; $OCH_3$); $^{13}$C NMR (75 MHz, Chloroform-d) δ 173.40, 168.46, 163.24, 163.15, 134.57, 132.61, 132.54, 130.83, 130.38, 130.12, 129.54, 129.19, 128.74, 127.26, 127.09, 124.61, 121.57, 120.51, 114.27, 113.92, 56.72, 55.64, 46.55, 25.86; HRMS (ESI): m/z $C_{29}H_{27}N_3O_8S_3+NH_4^+$: 659.1299 $[M+NH_4]^+$; molecular weight: 659.1300.

2.2. Preparation of N,N'-(naphthalene-1,4-diyl)bis(4-methoxy-N-(2-oxo-2-(2-oxothiazolidin-3-yl)ethyl)benzenesulfonamide) (pro1)

Compound 1 (0.5 g, 0.81 mmol) was dissolved in DMF (10 mL) at room temperature, and DCC (0.37 g, 1.79 mmol) and DMAP (0.22 g, 1.79 mmol) were added. After 30 min, thiazolidin-2-one (0.37 g, 3.60 mmol) was added, and the mixture was stirred for reaction overnight. After the reaction was complete, the reaction solution was poured into water and extracted with $Et_2O$ (20 mL×3). The organic phases were combined, dried over $Na_2SO_4$ and concentrated in vacuo. The crude product was purified by column chromatography to give a pure product as a white solid (0.368 g, 58% yield). $R_f$=0.42 (EA/PE 1:1); m.p. 234-235° C.; $^1$H NMR (300 MHz, DMSO-$d_6$) δ 8.28 (dd, J=6.9, 3.4 Hz, 2H; Ar—H), 7.57 (d, J=8.5 Hz, 4H; Ar—H), 7.10 (d, J=8.8 Hz, 4H; Ar—H), 7.03 (d, J=8.5 Hz, 4H; Ar—H), 4.23 (s, 4H; $CH_2$), 3.87 (s, 6H; $OCH_3$), 3.81 (s, 4H; $CH_2$), 3.01-3.06 (t, J=7.1 Hz, 4H; $CH_2$); $^{13}$C NMR (75 MHz, Chloroform-d) δ 173.57, 168.62, 163.32, 134.73, 132.71, 130.29, 128.91, 127.26, 124.77, 121.74, 114.44, 56.89, 55.81, 46.72, 26.03; HRMS (ESI): m/z $C_{34}H_{32}N_4O_{10}S_4+H^+$: 785.1074 $[M+H]^+$, molecular weight: 785.1074.

The synthetic method of Compound 1 is described in: M.-C. Lu, J.-A. Ji, Z.-Y. Jiang, Q.-D. You, the Keap1-Nrf2-ARE Pathway As a Potential Preventive and Therapeutic Target: An Update, *Med. Res. Rev.,* 36 (2016) 924-963.

Example 2. Pharmacokinetics of Target Compound

1. Pharmacokinetic Study

1.1. Drug Release Rate by HPLC

The target compound was dissolved in DMSO to give a 10 mM stock solution, which was then stored at −20° C. The final concentration was brought to 50 μM by adding the target compound (10 mM) to phosphate buffered saline (PBS) (10 mM, pH 7.4), and $H_2O_2$ was added. The solution was well vortexed, and then incubated at 37° C. Samples were taken at appropriate time intervals and analyzed by HPLC directly after injection, and the peak areas were recorded to calculate the percentage of the compound. The procedure was repeated three times. The following Agilent 1260 HPLC and DAD detectors were used: Agilent C18 column (4.6×150 mm, 3.5 μm); mobile phase: 70% methanol; flow rate: 0.5 mL/min. A standard curve of the compound was plotted against concentration.

1.2. Intracellular Drug Release by LC-MS

RAW 264.7 cells were cultured in a culture dish containing 10 mL of a medium for 24 h. Cells were stimulated with $H_2O_2$ (0.25 mM) for 12 h, then washed with the fresh medium, and treated with the 1 mM target compound for 12 h. Cells were washed with the fresh medium, and 1 mL of methanol was added to the cell pellet. The mixture was well vortexed, and then centrifuged at high speed for 10 min. The supernatant was immediately preserved at −80° C. for subsequent analysis. The analysis was performed by using a LC-MS/MS spectrometer (6410 Triple Quad LC/MS/MS, Agilent Technologies, Willington) provided with a chromatography column (Agilent C18 column, 4.6-150 mm, 3.5 μm), on which 5 μL of the sample was injected.

1.3. Assay for Physicochemical Properties and Cell Membrane Permeability

Through Avdeef-Bucher potentiometric titration, pKa and partition coefficients (log D, pH 7.4) were determined on a Gemini Profiler instrument (pION) according to the method of Avdeef and Tsinman. pH measurements were used to determine the intrinsic solubility.

Potential solubility data were obtained with a pSOL model 3 instrument (pION INC, Cambridge, Massachusetts, USA). Cell membrane permeability was determined on a PAMPA Explorer instrument (pION).

1.4. Stability Test (1) pH stability. PBS buffers with different pH values (pH 4-10) were prepared from a 0.1 M HCl solution and a 0.1 M NaOH solution. The prodrug pro2 (20 μM) was incubated in triplicate together with the PBS buffers of different pH at 37° C. After 24 h of incubation, the solutions were filtered and injected for direct sample analysis by HPLC, and the peak areas were recorded to calculate the percentage of compound.

(2) Stability in plasma. Samples (20 μM) of the prodrug pro2 were co-incubated in triplicate with mouse plasma at 37° C. at different time periods. Methanol was added to precipitate the proteins, and the samples were vortexed and then centrifuged at 12,000 rpm for 5 min. The supernatants were analyzed by HPLC and the peak areas were recorded.

(3) Stability in microsomes. Isolated liver microsomes (from CD-1 male rats and human males) were used to evaluate the stability of the compound in microsomes in vitro. Ketanserin was used as a reference compound. A liver microsome solution (20 mg/mL) was added to a microcentrifuge tube containing PBS at 37° C. and the mixture was shaken for 10 min prior to assay. Then a DMSO solution (0.5 mM) containing the test compound was added. At 0 min, pre-cooled acetonitrile was added followed by an NADPH stock solution (6 mM). The plates were pre-incubated at 37° C. for 5 min. The timer started upon the addition of the NADPH stock solution (6 mM) to the plates. At 5 min, 15 min, 30 min and 45 min, pre-cooled acetonitrile was added to the wells of the respective plates to stop the reactions. After the reaction was quenched, the plates were shaken on a shaker for 10 min and then centrifuged at 5000 rpm for 15 min. The supernatant from each well was transferred to a 96-well sample plate containing ultrapure water for LC-MS/MS analysis.

(4) Stability in artificial gastric and intestinal fluids. Artificial gastric and intestinal fluids were purchased from commercial suppliers. Samples of prodrug (20 μM) were incubated in triplicate with artificial gastric or intestinal fluids at 37° C. for different periods of time. The enzyme protein was precipitated by adding methanol, and the samples were vortexed and then centrifuged at 5000 rpm for 5 min. The supernatants of the samples were analyzed by HPLC and the peak areas were recorded. All chromatographic conditions were as described above.

2. Results 2.1. Validation of Release of Active $H_2O_2$-Responsive Drug

Figure 1:
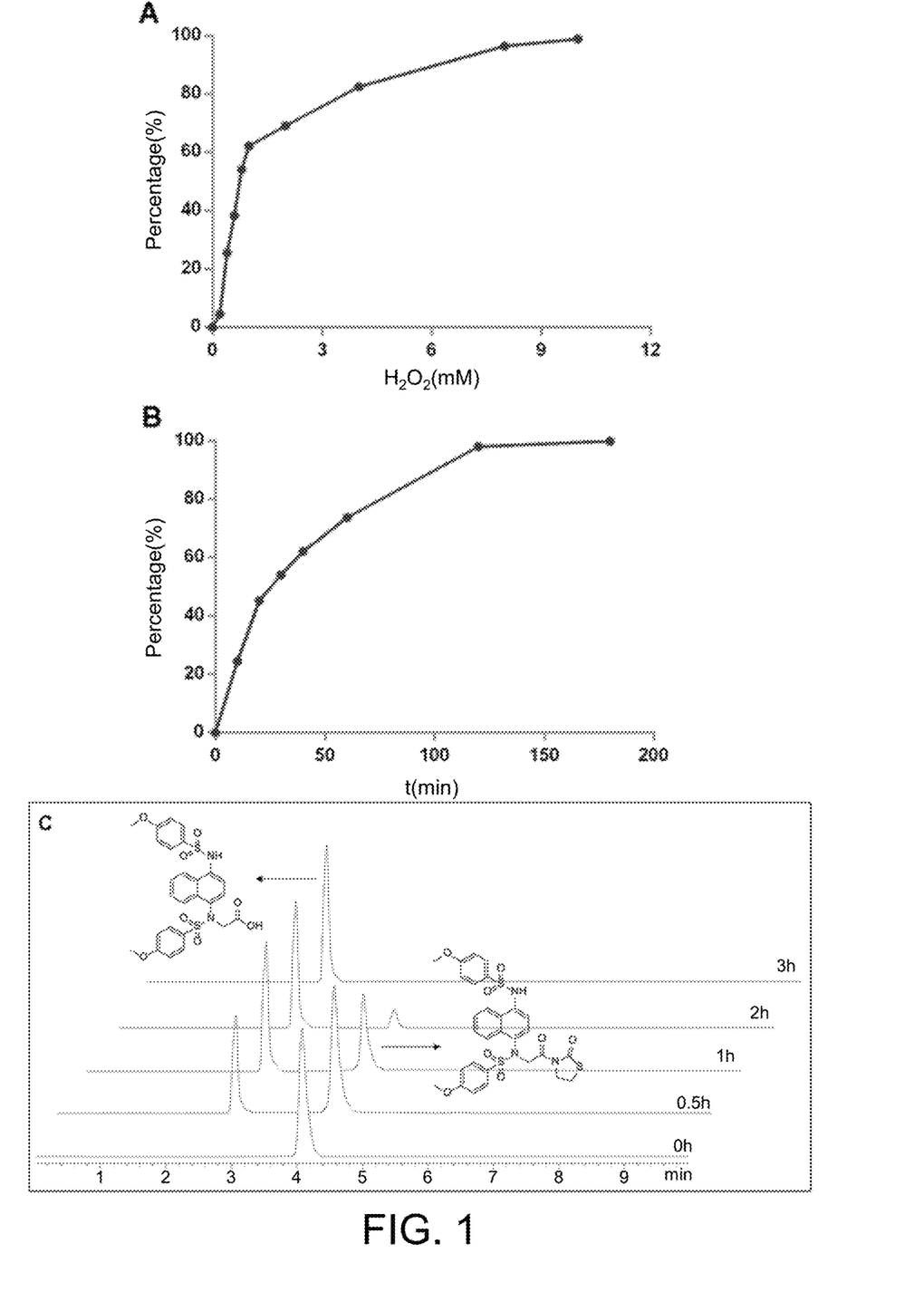
FIG. 1 shows the H$_2$O$_2$ activation of pro2, wherein (A) of FIG. 1 shows the activation of pro2 at different concentrations of H$_2$O$_2$, (B) of FIG. 1 shows a release curve of pro2 over time, and (C) of FIG. 1 shows a chromatogram of $H_2O_2$ (10 equiv.) activation of pro2 in a DMSO/PBS (1/1, v/v) mixture by UPLC-MS-PDA.

By HPLC, a $H_2O_2$ concentration-dependent release of the active parent compound 2 was observed and a release of no less than 50% of the active parent compound 2 was observed at a $H_2O_2$ concentration of 0.8 mM after 24 h of incubation in the presence of the prodrug pro2 ((A) of FIG. 1). After treatment with 10 mM $H_2O_2$, the prodrug pro2 was activated with prolonged incubation time and the active parent compound 2 was completely released within 3 h (HPLC-determined conversion >98%, (B) of FIG. 1 and (C) of FIG. 1). However, the hydrolyzed prodrug pro1 containing two thiazolidinone precursor moieties only produced a free carboxylic acid compound as identified by UPLC/HRMS in the presence of $H_2O_2$, and no production of the active parent compound 1 could be observed at 12 h.

$H_2O_2$-responsive activation of pro2 was further examined in living cells. Mouse macrophages (RAW264.7) were stimulated with $H_2O_2$ for 24 h to induce intracellular production of ROS, and then the medium was replaced with a fresh medium. The prodrug pro2 (1 mM) was added to stimulated or unstimulated cells for incubation and cell lysates were analyzed by LC-MS. The peak for parent compound 2 was not observed in the unstimulated cells, whereas a clear signal for the parent compound 2 was observed in the stimulated cell lysates. The results demonstrate that the prodrug pro2 can be absorbed into cells and converted into the parent compound 2 in the presence of intracellular $H_2O_2$.

2.2. Evaluations of Stability, Physicochemical Properties and Permeability

Figure 2:
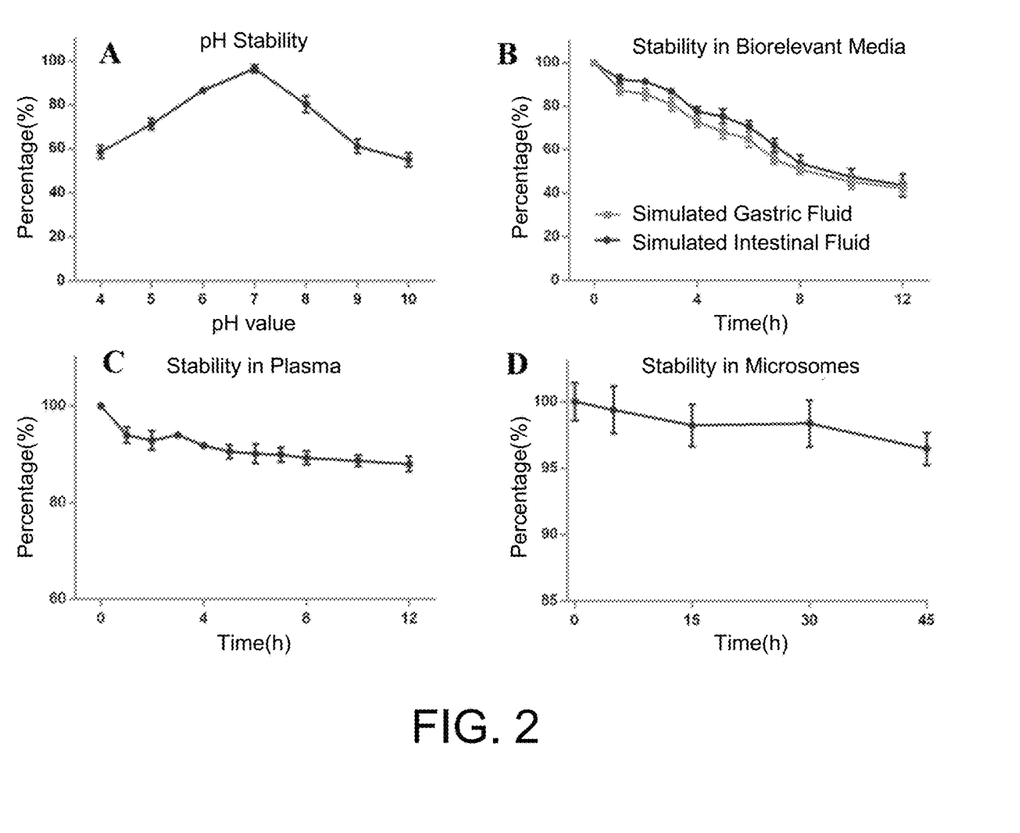
FIG. 2 shows stability curves of pro2, wherein (A) of FIG. 2 shows a stability curve of pro2 at different pH (4-10), (B) of FIG. 2 shows stability curves of pro2 in SGF and SIF, (C) of FIG. 2 shows a stability curve of pro2 in rat plasma, and (D) of FIG. 2 shows a stability curve of pro2 in liver microsomes.

The stability of the target compound in different relevant physiological conditions was evaluated. It was observed that the prodrug pro2 was hydrolytically stable in PBS solutions at different pH of 4-10 ((A) of FIG. 2) and relatively stable in biorelevant media including simulated gastric fluid (SGF) and simulated intestinal fluid (SIF), with >50% remaining after 8 h ((B) of FIG. 2). In addition, pro2 is very stable in rat plasma ((C) of FIG. 2) and in co-incubation with human and rat liver microsomes ((D) of FIG. 2), showing good pharmacokinetics.

Physical properties related to membrane permeability of the prodrug pro2 and parent compound 2 are shown in Table 1. The pKa and log $D_{pH=7.4}$ of the active parent compound 2 were 4.31 and 1.88, respectively, while the pKa and log $D_{pH=7.4}$ of pro2 were 4.53 and 2.34, respectively. These results demonstrate that the prodrug pro2 is less ionizable and polar than the active parent compound 2, and thus the cell membrane permeability of the prodrug pro2 is enhanced. Subsequently, the permeability of cell membranes was measured by standard parallel artificial membrane permeability assay (PAMPA). The permeability coefficient (Pe) for the active parent compound 2 was $0.80 \cdot 10^{-6}$ cm/s and the Pe for pro2 was $6.35 \times 10^{-6}$ cm/s, demonstrating that pro2 passes through cell membranes more easily by passive transport mechanism.

TABLE 1

Physical properties related to membrane permeability of prodrug pro2 and parent compound 2

| Compound | pKa | LogD at pH 7.4 | Aqueous solubility at pH 7.4 (μg/mL) | Pe at pH 7.4 ($10^{-6}$ cm/s) |
|---|---|---|---|---|
| Pro2 | 4.53 | 2.34 | 879.6 | 6.35 |
| 2 | 4.31 | 1.88 | 428.2 | 0.80 |

Example 3. Evaluation of Anti-Inflammatory Activity of Target Compound

1. Anti-Inflammatory Activity Assay 1.1. LPS-Induced ROS Production (DCFH-DA Method)

RAW264.7 cells were pre-treated with LPS at 0.3125, 0.625, 1.25, 2.5, 5, 10, 20 ng/mL in humidified air containing 5% $CO_2$ at 37° C. for 8 h. As a control group, cells were cultured in the same medium without addition of LPS. The cells were incubated in DCFH-DA (10 μM) at 37° C. for 30 min and then washed 3 times before being harvested and resuspended in PBS. Fluorescence was detected using a Thermo Scientific microplate reader.

1.2. ARE-Luciferase Activity Assay

HepG2-ARE-C8 cells were plated in a 96-well plate at a density of $4 \times 10^4$ cells/well and incubated overnight. The cells were then incubated with different concentrations of the test compound, with DMSO as a negative control and a luciferase cell lysis agent as a blank control. After 12 h of treatment, the medium was removed and 100 μL of pre-cooled PBS was added to each well to wash the cells. PBS was then removed and 30 μL of the luciferase cell lysis agent was added. After 15 min of lysis on ice, the cells were harvested and centrifuged, and 20 μL of the supernatant was taken for luciferase activity assay according to the protocol provided by the manufacturer (Promega, Madison, WI). The luciferase activity was measured by Luminoskan Ascent (Thermo Scientific, USA). The assay was performed in triplicate and the inductivity fold was calculated by comparing with the control.

1.3. Fluorescent Real-Time Quantitative PCR

The procedures were performed according to the real-time quantitative RT-PCR experimental procedures reported previously (Z. Jiang, M. Lu, Q. D. You, Discovery and Development of Kelch-like ECH-Associated Protein 1: Nuclear Factor Erythroid 2-Related Factor 2 (KEAP1:NRF2) Protein-Protein Interaction Inhibitors: Achievements, Challenges and Future Directions, *J. Med. Chem.*, 59 (2016) 10837-10858). The primers used for qRT-PCR were as follows: Nrf2 (forward primer: AACCACCCT-GAAAGCACGC, reverse primer: TGAAATGCCG-GAGTCAGAATC); HO-1 (forward primer: ATGGCCTCCCTGTACCACATC, reverse primer: TGGTGCGCTCAATCTCCTCCT); NQO-1 (forward primer: CGCAGACCTT-GTGATATTCCAG, reverse primer: CGTTTCTTCCATCCTTCCAGG); GCLM (forward primer: TTGGAGTTGCACAGCTGGATTC, reverse primer: TGGTTTTACCTGTGCCCACTG).

1.4. Western Blot

Anti-Nrf2 (ab62352) and anti-IL-1β (ab45692) antibodies were purchased from Abcam Technology (England). Anti-HO-1 (SC-136960) and anti-NQO1 (SC-271116) antibodies were purchased from Santa Cruz Biotechnology (California, USA). Anti-β-Actin (60008-1-Ig) and anti-GCLM (14241-1-AP) antibodies were purchased from Proteintech Group (USA). Cell sampling and western blot were performed as previously reported (M.-C. Lu, J.-A. Ji, Y.-L. Jiang, Z.-Y. Chen, Z.-W. Yuan, Q.-D. You, Z.-Y. Jiang, An inhibitor of the Keap1-Nrf2 protein-protein interaction protects NCM460 colonic cells and alleviates experimental colitis, *Sci. Rep.*, 6 (2016) 26585).

1.5. IL-1β, IL-18, IL-6, TNF-α and NO Assays

IL-1β (IL-1β (m) ELISA kit, EK0394, Boster), IL-18 (IL-18 (m) ELISA kit, EMC011, NeoBioscience), IL-6 (IL-6 (m) ELISA kit EK0411, Boster), TNF-α (TNF-α (m) ELISA kit, EK0527, Boster) and NO (nitrate/nitrite assay kit, S0023, Beyotime, China) were tested using commercially available kits according to the manufacturer's instructions.

1.6. In Vivo Pharmacokinetic Study

Six male SD rats weighing about 260 g were used, with 3 rats for PO study and the other 3 rats for IV study. The test compound was dissolved in normal saline with a cosolvent to prepare a solution before the study. For the PO study, animals were administered orally (10 mg/kg). For the IV study, the test compound (3 mg/kg) was administered by intravenous injection. Blood was sampled at 0.0833, 0.25, 0.5, 1, 2, 4, 6, 8, 24 h in groups IV and PO. The blood samples were preserved on ice and then centrifuged at 2000 rpm and 4° C. for 10 min for separating plasma. The plasma samples were transferred and stored at −80° C. before analysis by LC-MS/MS.

1.7. Establishment of LPS-Induced Mouse Acute Inflammation Model

Female C57BL/6 mice (6-8 weeks old, 18-20 g in weight) were acclimatized with drinking water for 2 days, and were randomized to eight groups: (A) control group (n=3); (B) LPS (Sigma-Aldrich, St. Louis, No. L4130) model group (300 μg/kg/day, n=8); (C) LPS (300 μg/kg/day)+pro2 low-dose (10 mg/kg/day) group (n=8); (D) LPS (300 μg/kg/day)+pro2 high-dose (40 mg/kg/day) group (n=8); (E) LPS (300 μg/kg/day)+active parent compound 2 high-dose (40 mg/kg/day) group (n=8); (F) LPS (300 μg/kg/day)+dexamethasone low-dose (10 mg/kg/day) group (n=8); (G) pro2 high-dose (40 mg/kg/day) group (n=3); and (H) active parent compound 2 high-dose (40 mg/kg/day) group (n=3). Animals of groups A, G and H were given IP injections of 500 μL of normal saline each time (on days −3, −2 and −1). All LPS-stimulated mice were IP-injected with 500 μL of LPS (on days −3, −2 and −1), and 4 h after the injection the mice were given corresponding compound treatment (on days −3, −2 and −1). Animals were sacrificed (day 0) 24 h after the last dose of the compound to collect the serum, and the levels of cytokine IL-1β, IL-6, TNF-α and IFN-γ in the serum were determined by ELISA.

Figure 3:
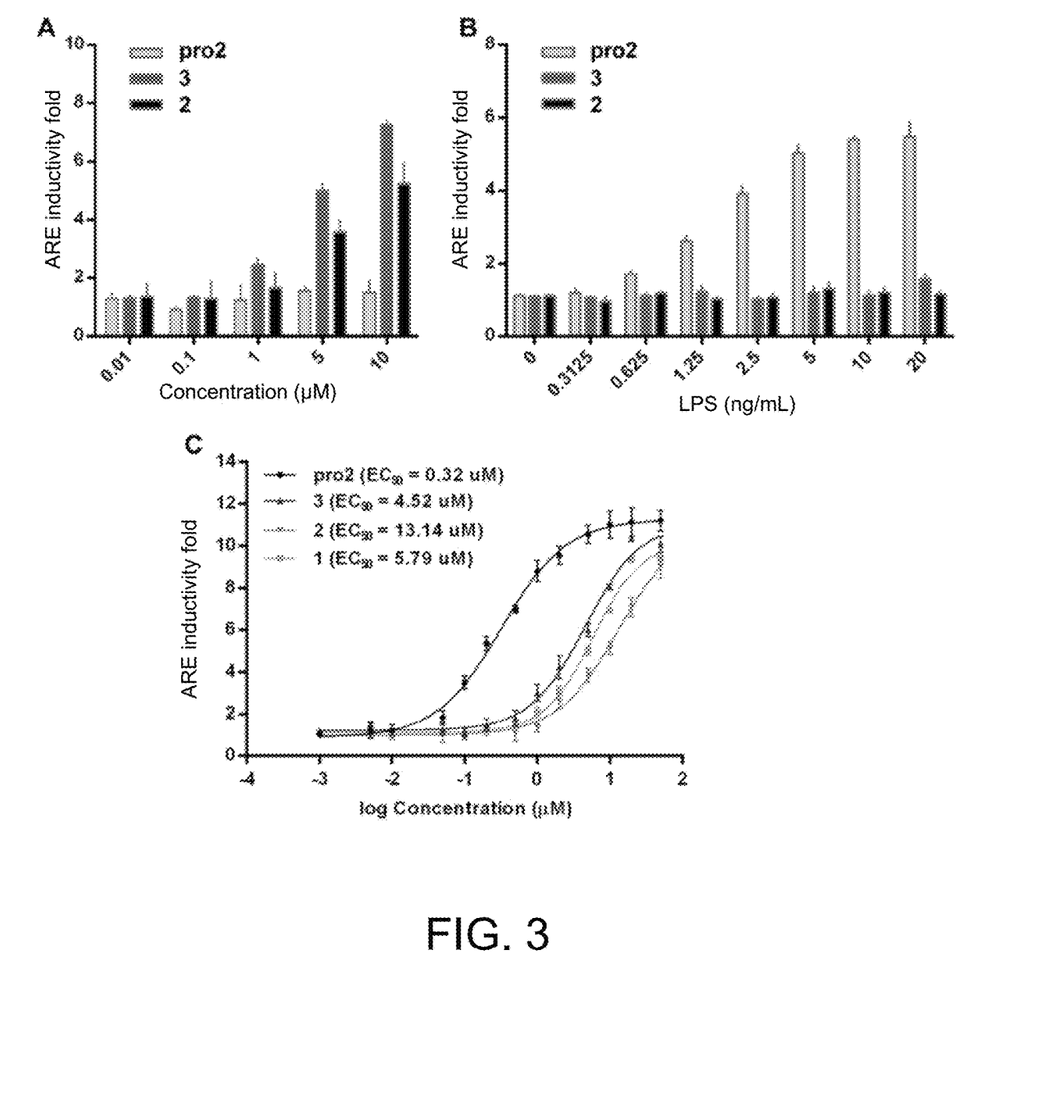
FIG. 3 shows comparisons in LPS inductivity and selectivity, wherein (A) of FIG. 3 shows the ARE inductivity in HepG2-ARE-C8 cells, (B) of FIG. 3 shows the ARE inductivity of pro2 in RAW264.7 cells at different concentrations of LPS, and (C) of FIG. 3 shows $EC_{50}$ curves of the ARE inductivity.

2. Results 2.1. Targeted Activation of Prodrugs by ROS Derived from Inflammation Cells were evaluated for Nrf2 activity status using Nrf2/ARE luciferase reporter assay, and a methyl ester prodrug 3 that does not respond to cellular ROS was used as a non-selective control to prove the selectivity of the response of pro2 to ROS. As shown in (A) of FIG. 3, both the methyl ester prodrug 3 and active parent compound 2 can induce ARE activity in a concentration-dependent manner. The methyl ester prodrug 3 demonstrated higher ARE inductivity compared to the active parent compound 2, probably because the methyl ester group has better cell membrane permeability. However, pro2 remained almost inactive even at the highest concentration, suggesting that pro2 is stable and does not affect the Nrf2-ARE system in physiological conditions.

To simulate a high ROS microenvironment similar to inflammation, cells were exposed to lipopolysaccharide (LPS), a widely used inflammation inducer that can enhance the production of intracellular ROS. The data indicate that the intracellular ROS level may be raised with increasing LPS concentration. Cells were stimulated with different concentrations of LPS prior to administration (200 nM). As shown in (B) of FIG. 3, the ROS derived from inflammation can active the prodrug, and the inductivity of Nrf2-ARE exhibited an LPS concentration-dependent increase, while no marked changes in the active parent compound 2 and methyl ester prodrug 3 were observed. The ARE inductivity of pro2 under LPS stimulation was then investigated more conveniently by measuring its $EC_{50}$ value. As shown in (C) of FIG. 3, the $EC_{50}$ value (4.52 μM) for the methyl ester prodrug 3 was lower than those of the parent compound 1 and 2, indicating that the prodrug strategy effectively improved the drug-like properties of the bioactive molecule. Pro2 demonstrated the lowest $EC_{50}$ value (0.32 μM) among these, and it is noteworthy that it was more effective than CPUY192002 having two carboxyl groups. In conclusion, the thiazolidinone-based prodrug pro2 can be selectively activated by LPS-induced ROS, and activates the Nrf2-ARE system at a much lower concentration than the parent drug.

2.2. Prodrug Activating Nrf2-ARE-Regulated Antioxidant System in RAW264.7 Cells

Figure 4:
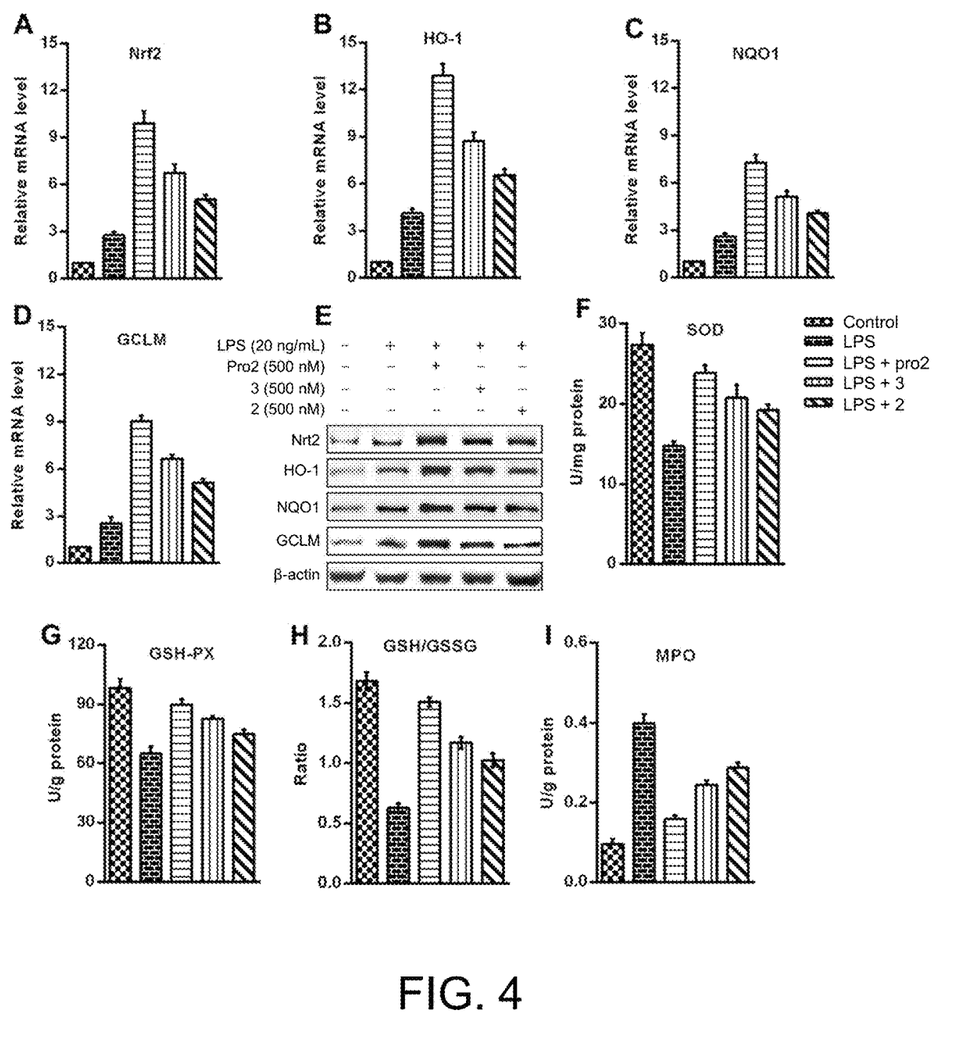

To determine the effect of pro2 on Nrf2-ARE-driven gene transcription, mRNA levels of Nrf2 and three downstream genes, HO-1, NQO1 and GCLM, were examined ((A) of FIG. 4 to (D) of FIG. 4). Real-time quantitative PCR (qRT-PCR) analyses showed that exposure of RAW264.7 cells to 20 ng/mL LPS for 8 h slightly increased the transcription of Nrf2 and downstream genes. The addition of 500 nM pro2 greatly enhanced the transcription over the parent drug 2 and methyl ester prodrug 3 at the same concentration. The protein levels of the above genes were determined by western blot. Consistent with the mRNA levels of these genes, the result for pro2 suggested that pro2 significantly increased levels of Nrf2 and downstream antioxidant enzyme, and was more effectively than parent drug 2 and its methyl ester prodrug 4 at the same concentration ((E) of FIG. 4). These results demonstrated that pro2 can significantly enhance the activation of the Nrf2-ARE system on a cellular level at a low concentration.

Subsequently, to investigate the effect of pro2 on antioxidant capacity in inflammatory conditions, the activities of superoxide dismutase (SOD) and glutathione peroxidase (GPx) were examined. RAW264.7 cells were treated with LPS (20 ng/mL) alone, and it is found that a significant reduction occurred in SOD and GSH-Px activity ((F) of FIG. 4 and (G) of FIG. 4), and treatment with pro2 restored the SOD and GSH-Px activity significantly, whereas the parent compound 2 and its methyl ester analog were much less effective. In addition, the GSH/GSSG ratio and myeloperoxidase (MPO) activity were also examined, which are two important markers indicating oxidative stress. Exposure to LPS resulted in a dramatic decrease in the GSH/GSSG ratio and a dramatic increase in MPO activity, indicating that LPS can cause oxidative stress, while addition of pro2 can return markers to near normal. The parent drug 2 and its methyl ester analog exhibited a similar trend but much lower activity than the prodrug pro2 ((H) of FIG. 4 and (I) of FIG. 4).

Figure 5:
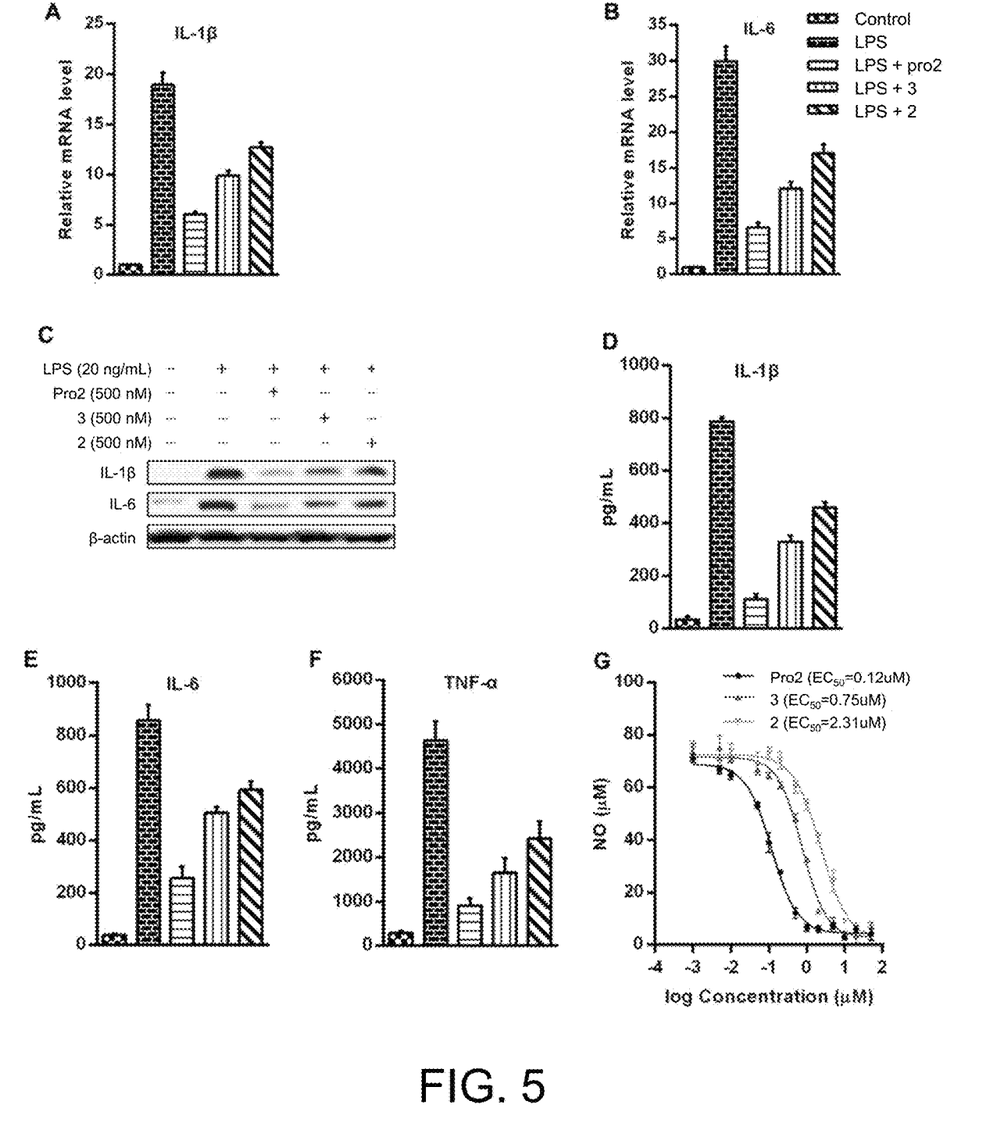

2.3. Prodrug Reducing LPS-Induced Inflammatory Factor Production in RAW264.7 Cells Activation of Nrf2 has been demonstrated as an effective method of alleviating inflammation. First, mRNA levels of IL-1β and IL-6, which can be directly inhibited by Nrf2, were measured. After stimulation with 20 ng/mL LPS for 8 h, the mRNA transcription for IL-1β and IL-6 in RAW264.7 cells was significantly increased. Treatment with the parent compound 2 or methyl ester prodrug 3 can inhibit transcription of IL-1β and IL-6 to some extent in RAW264.7 cells. Notably, treatment with pro2 can significantly inhibit the induction by pro-inflammatory genes ((A) of FIG. 5 and (B) of FIG. 5). Consistent with the results of the PCR analysis, the parent compound 2 and methyl ester prodrug 3 demonstrated mild and moderate inhibitory effects on LPS-induced IL-1β and IL-6 protein expression, respectively, but the same concentration of pro2 almost completely inhibited the expression of pro-inflammatory factors on protein level ((C) of FIG. 5).

Then, several inflammatory mediators closely related to ROS, including IL-1β, IL-6, TNF-α and NO, were further evaluated. Compared to the control group, the LPS treatment groups had significant increases in all inflammatory factors, and pro2 exhibited significant advantages in inhibiting production of IL-1β, IL-6, and TNF-α ((D) of FIG. 5 to (F) of FIG. 5). Pro2 also greatly reduced the extracellular NO concentration increase caused by LPS stimulation, with the $EC_{50}$ being 0.12 μM, while both the parent compound 2 and its methyl ester prodrug 3 showed higher $EC_{50}$ values ((G) of FIG. 5). These results clearly demonstrated the anti-inflammatory effect of pro2 and confirmed the cytoprotective effect of pro2 on LPS-stimulated RAW264.7 cells.

2.4. In Vivo Efficacy of ROS-Activated Prodrugs Against LPS-Induced Inflammation After the ROS-responsive activation of Nrf2 by pro2 in living cells was confirmed, the therapeutic potential of pro2 in vivo was also investigated. To explore the feasibility of oral administration of the thiazolidinone prodrug pro2, the IV and PO pharmacokinetics of pro2, as well as the oral pharmacokinetics were evaluated, with the bioavailability being 68.1% and the half-life being 2.09±0.93 h (Table 2), suggesting that pro2 might be an effective drug for oral administration.

TABLE 2

| In vivo physicochemical properties of pro2 | | |
|---|---|---|
| | P.O. (10 mg/kg) | I.V. (2 mg/kg) |
| $T_{1/2}$ (h) | 2.09 ± 0.93 | 4.41 ± 3.01 |
| $T_{max}$ (h) | 0.67 ± 0.29 | — |
| $C_{max}$ (ng/mL) | 2753 ± 15.3 | — |
| $AUC_{0-t}$ (ng · h/mL) | 6203 ± 248 | 1842 ± 363 |
| $AUC_{0-\infty}$ (ng · h/mL) | 6315 ± 273 | 1854 ± 366 |
| Vz_F (L/kg) | 4.79 ± 2.17 | 6.44 ± 4.09 |
| Cl_F (mL/min/kg) | 26.4 ± 1.14 | 18.5 ± 3.9 |
| MRT (h) | 1.82 ± 0.35 | 1.25 ± 0.30 |

Figure 6:
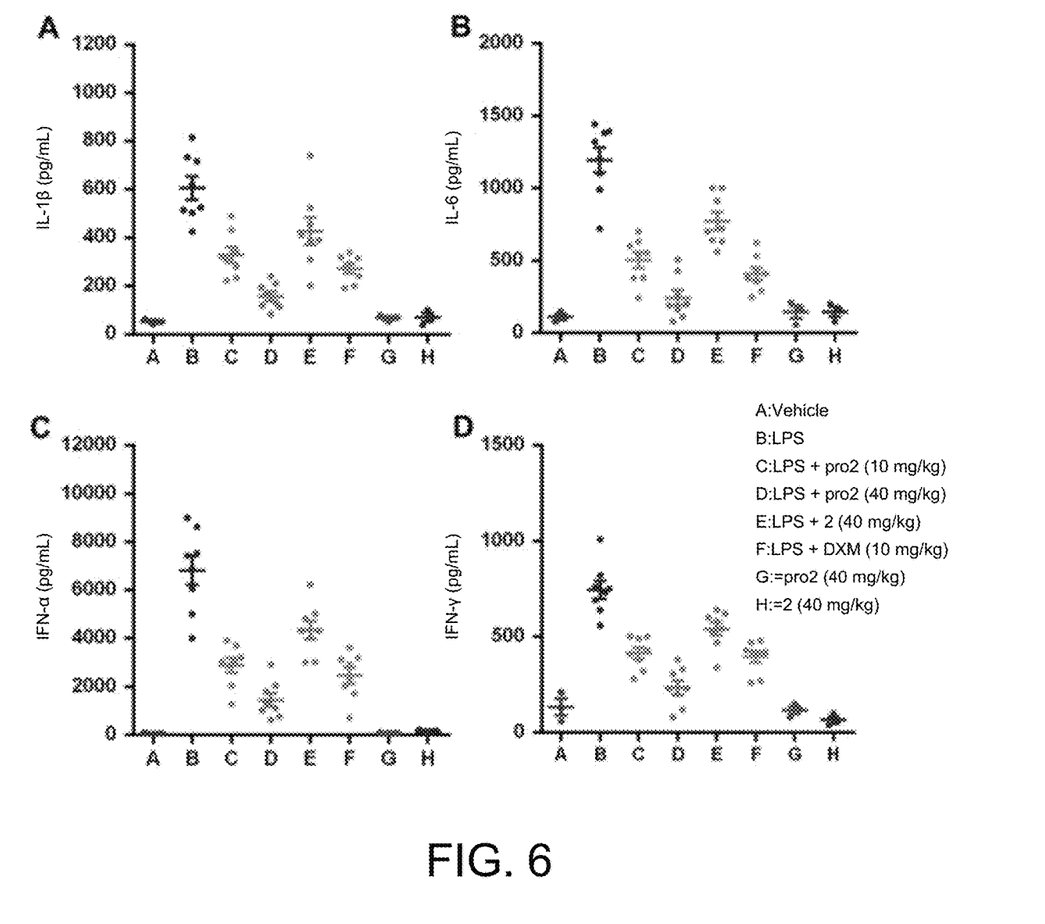

A mouse acute inflammation model was induced by LPS for evaluating the anti-inflammatory effects in vivo. The LPS model group (300 μg/kg) had significantly increased pro-inflammatory cytokines including IL-1β, IL-6, TNF-α and IFN-γ in mouse serum, and the dexamethasone treatment group (10 mg/kg) had attenuated inflammatory response. Orally administered active parent compound 2 (40 mg/kg) demonstrated moderate anti-inflammatory activity, which was lower than that of dexamethasone. Pro2 showed comparable therapeutic effect to dexamethasone at the same dose (10 mg/kg), whereas a high dose of pro2 showed stronger effect, suggesting a dose-dependent effect for pro2 (as shown in (A) of FIG. 6 to (D) of FIG. 6). These results suggest that the thiazolidinone prodrug, synthesized based on ROS response design, is a Keap1-Nrf2 PPI inhibitor for oral administration and can be used for treating oxidative stress-related inflammation.

In the present application, a novel ROS activation-ROS clearance therapy was explored by studying an $H_2O_2$-responsive prodrug of Keap1-Nrf2 inhibitor. The present application proved that inhibitors lose activity in disrupting the Keap1-Nrf2 interaction, and that inflammation-derived ROS can release active species, which exert anti-inflammatory effects in cells and in vivo inflammation models. This is a proof-of-concept system for ROS activation-ROS clearance therapy, and is also the first example of a $H_2O_2$-responsive prodrug suitable for oral administration.

A novel ROS-responsive antioxidant prodrug pro2 is synthesized by using a $H_2O_2$-responsive thiazolidinone moiety to modify a key carboxyl pharmacophore in a Keap1-Nrf2 inhibitor. $H_2O_2$ produced in inflammatory cells can trigger carboxyl group production, thereby producing effective Keap1-Nrf2 inhibitors to activate Nrf2-regulated antioxidant systems in target cells. The prodrug designed based on carboxyl groups can not only release the parent drug to activate Nrf2 at a high concentration of $H_2O_2$, but also improve the physicochemical properties and cell membrane permeability of the parent drug. Further cellular studies have shown that prodrugs can remain inactive in physiological conditions and are more effective than the parent drug in inflammatory conditions. In addition, the thiazolidinone-based drugs exhibit good stability in various physiological conditions and have PK properties suitable for oral administration. Finally, in vivo therapeutic activity was proved by oral administration of the prodrug in an LPS-induced acute inflammation model. These studies proved that $H_2O_2$-activated prodrugs can simultaneously implement targeted activation of Nrf2 and enhancement of therapeutic efficacy in vivo. Pro2 is the first H$_2$O$_2$-responsive prodrug suitable for oral administration, and is expected to be used clinically by virtue of druggability.

The above-described embodiments are intended to illustrate the material content of the present invention, but those skilled in the art should be appreciated that the scope of the present invention is not be limited to such embodiments.

What is claimed is:

1. A prodrug pro2 of hydrogen peroxide-responsive Keap1-Nrf2 PPI inhibitor having the following structural formula:

pro2

2. A method for preparing a prodrug pro2, wherein a synthetic route is as follows:

-continued wherein, the reagents and conditions in each step are as follows:
(b) Pd/C, H$_2$, THF, rt, 4 h;
(c) 4-methoxybenzenesulfonyl chloride, Na$_2$CO$_3$, THF, 0° C., 2 h;
(d) 4-methoxybenzenesulfonyl chloride, toluene, pyridine, 100° C., 2 h;
(e) DMF, K$_2$CO$_3$, ethyl bromoacetate, rt, 3 h;
(f) LiOH, MeOH, H$_2$O, 2 h; and
(g) thiazolidin-2-one, DMAP, DCC, DMF, rt, 6 h.

3. The method according to claim 2, wherein compound 4 is synthesized by the following route:

wherein, the reagents and conditions in the step (a) are as follows: NH$_2$OH·HCl, 95% ethanol, MeOH, 60° C., and 2 h.

4. A method for preparing a prodrug pro2 in preparing an anti-inflammatory drug, the prodrug pro2 having the following structural formula:

5. The method according to claim 4, wherein the drug increases levels of Nrf2 and downstream antioxidant enzymes, and enhances the activation of the Nrf2-ARE system at a cellular level.

6. The method according to claim 4, wherein the drug inhibits expression of pro-inflammatory factors IL-1β and IL-6 at a protein level.

7. The method according to claim 4, wherein the drug is for oral administration.

* * * * *

SEQUENCE LISTING

```
<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
aaccaccctg aaagcacgc                                          19

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
tgaaatgccg gagtcagaat c                                       21

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
atggcctccc tgtaccacat c                                       21

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
tggtgcgctc aatctcctcc t                                       21

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
cgcagacctt gtgatattcc ag                                      22

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
cgtttcttcc atccttccag g                                       21
```

```
<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
ttggagttgc acagctggat tc                                       22

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8 tggtttacc tgtgcccact g                                         21
```